(12) United States Patent
Sebastian et al.

(10) Patent No.: US 8,062,218 B2
(45) Date of Patent: Nov. 22, 2011

(54) SURGICAL ACCESS INSTRUMENT

(75) Inventors: Kelli N. Sebastian, Arlington, TN (US);
Dimitri K. Protopsaltis, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 442 days.

(21) Appl. No.: 12/394,446

(22) Filed: Feb. 27, 2009

(65) Prior Publication Data
US 2010/0222644 A1    Sep. 2, 2010

(51) Int. Cl.
*A61B 1/32* (2006.01)
(52) U.S. Cl. .......................... 600/229; 600/232
(58) Field of Classification Search ................ 600/184, 600/201–246
See application file for complete search history.

(56) References Cited

U.S. PATENT DOCUMENTS

| | | | |
|---|---|---|---|
| 3,858,578 A | 1/1975 | Milo | |
| 4,945,896 A * | 8/1990 | Gade | 600/202 |
| 5,348,259 A | 9/1994 | Blanco et al. | |
| 5,513,827 A | 5/1996 | Michelson | |
| 5,616,117 A * | 4/1997 | Dinkler et al. | 600/232 |
| 5,662,300 A | 9/1997 | Michelson | |
| 6,120,436 A | 9/2000 | Anderson et al. | |
| 6,758,809 B2 * | 7/2004 | Briscoe et al. | 600/229 |
| 6,866,628 B2 | 3/2005 | Goodman et al. | |
| 6,945,933 B2 | 9/2005 | Branch et al. | |
| 7,097,612 B2 | 8/2006 | Bertolero et al. | |
| 7,311,664 B2 | 12/2007 | Goodman et al. | |
| 7,473,222 B2 | 1/2009 | Dewey et al. | |
| 2001/0041827 A1 | 11/2001 | Spence et al. | |
| 2002/0099268 A1 | 7/2002 | Paul et al. | |
| 2003/0195393 A1 | 10/2003 | Goodman et al. | |
| 2003/0229271 A1 | 12/2003 | Briscoe et al. | |
| 2004/0030223 A1 | 2/2004 | Calafiore et al. | |
| 2004/0171917 A1 | 9/2004 | Paul et al. | |
| 2004/0176665 A1 * | 9/2004 | Branch et al. | 600/210 |
| 2004/0225195 A1 | 11/2004 | Spence et al. | |
| 2004/0230191 A1 | 11/2004 | Frey et al. | |
| 2005/0101840 A1 | 5/2005 | Goodman et al. | |
| 2005/0192485 A1 | 9/2005 | Branch et al. | |
| 2006/0106288 A1 | 5/2006 | Roth et al. | |
| 2006/0122462 A1 | 6/2006 | Roth et al. | |
| 2008/0108878 A1 | 5/2008 | Goodman et al. | |
| 2008/0183046 A1 * | 7/2008 | Boucher et al. | 600/232 |
| 2009/0259107 A1 * | 10/2009 | Crenshaw et al. | 600/202 |

FOREIGN PATENT DOCUMENTS

WO    2007130609 A2    11/2007

OTHER PUBLICATIONS

International Search Report and Written Opinion for US Application PCT/US2010/025401 mailed on Apr. 13, 2010.

* cited by examiner

*Primary Examiner* — Cris L Rodriguez
*Assistant Examiner* — Edward Moran

(57) ABSTRACT

Embodiments of the invention include instruments and methods for providing surgical access to a surgical site. Some embodiments include a flexible arm that adjustably holds a retractor blade to enable access to the surgical site.

13 Claims, 10 Drawing Sheets

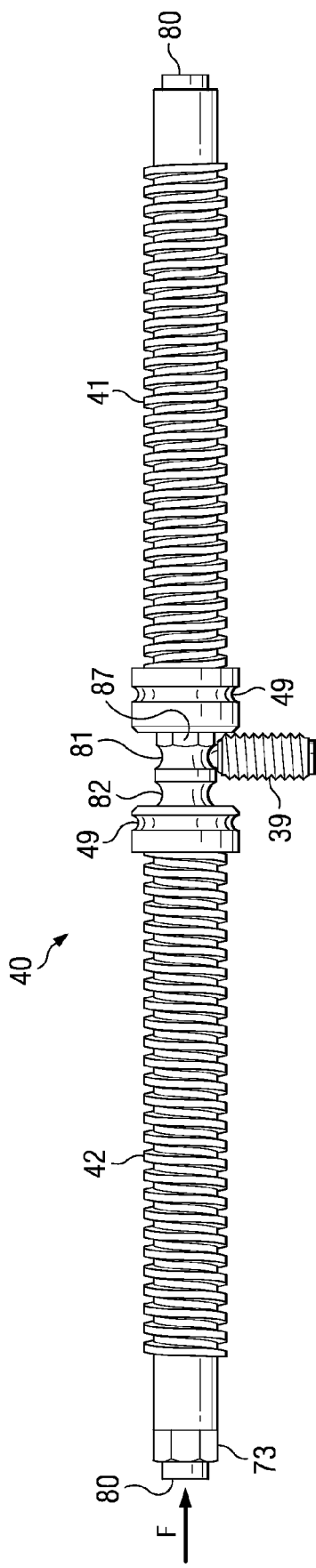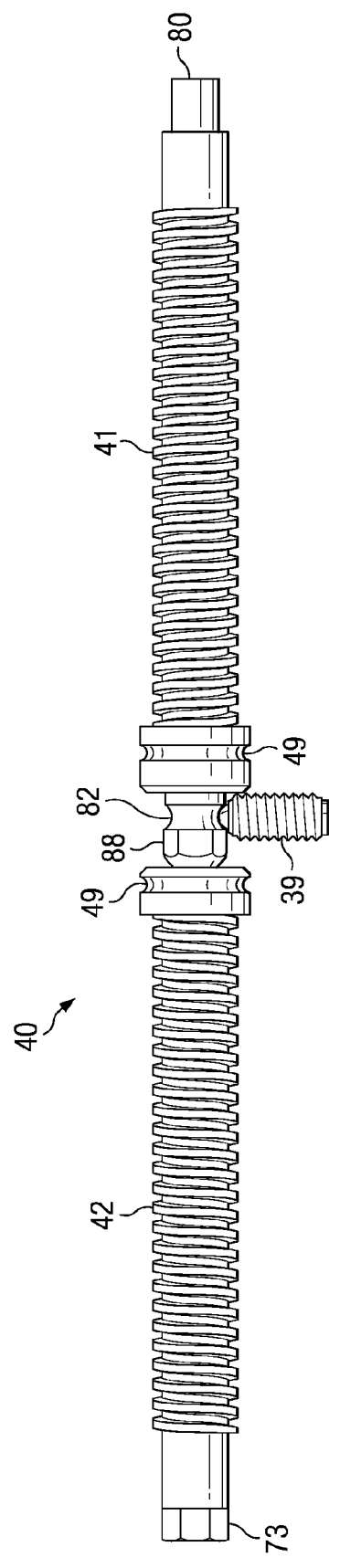

SURGICAL ACCESS INSTRUMENT

FIELD OF THE INVENTION

The present invention relates generally to the field of instruments for providing access during surgical procedures, and more particularly relates to retractor instruments for enabling access to a surgical site and shielding tissue during a surgical procedure.

BACKGROUND

Surgical procedures have generally become less disruptive to peripheral tissues as surgical techniques have progressed. Traditional surgical procedures used to treat tissues through incisions have often been very disruptive to peripheral tissues. Such procedures may include incisions through the skin, muscles, vessels, nerves, and other tissues, and may include long and deep incisions. Traditional procedures may include retractors that are either larger than is necessary to effectively perform a procedure or that are cumbersome to operated and therefore require longer periods of retraction than is necessary to perform a procedure. Traditional procedures, consequently, may lead to more trauma to peripheral tissues, more pain, and more lengthy and expensive recoveries. Cumbersome equipment that results in longer operating times may also lead to greater hospital, surgical staff, and physician expenses.

Modern surgical instruments and techniques have enabled less invasive and more expedient access to surgical sites. By way of non-limiting example, less invasive surgical instruments and techniques have been used in spinal surgery to separate and progressively dilate and retract tissues rather than to sever and retract the tissues. Developments in less invasive surgical instruments and methods have been significant, but there remains a need for enhancement of instruments and methods. Enhanced instruments and methods may include features that enable one or more of improvements to the efficiency, speed, access capability, or size of an instrument used in one or more methods.

Although particular embodiments of the surgical instruments and methods are described herein in association with particular spinal surgical procedures and surgical approaches, certain instruments and methods may be equally effective in other surgical procedures in the spine or in other areas of the anatomy.

SUMMARY

One embodiment of the invention is a surgical access instrument. The surgical access instrument may include a flexarm retractor with a base, a first retractor appendage coupled to the base wherein the first retractor appendage has a length and lateral sides along its length, a flexible arm coupled to the base at a proximal end of the flexible arm such that a distal end of the flexible arm is movable relative to the base, and a second retractor appendage coupled to the flexible arm at the distal end of the flexible arm wherein the first retractor appendage has a length and lateral sides along its length. The surgical access instrument may also include a transverse retractor coupled to the base of the flexarm retractor. The transverse retractor may include an assembly with a frame, a threaded shaft rotatably coupled with the frame, a first carriage coupled with the threaded shaft that is configured to translate along the threaded shaft when the shaft is turned, and a second carriage coupled with the threaded shaft that is configured to translate along the threaded shaft when the shaft is turned. Embodiments of the transverse retractor may also include a first transverse retractor appendage coupled with the first carriage, wherein the first retractor appendage has a length and lateral sides along its length, and a second transverse retractor appendage coupled with the second carriage, wherein the second retractor appendage has a length and lateral sides along its length. In some embodiments, the first retractor appendage, the second retractor appendage, the first transverse retractor appendage, and the second transverse retractor appendage are configured to be aligned substantially along their respective lengths and an access portal to the surgical site is formed among a lateral side of the first retractor appendage, a lateral side of the second retractor appendage, a lateral side of the first transverse retractor appendage, and a lateral side of the second transverse retractor appendage.

An embodiment of the invention is a flexible retractor for holding back tissue near a surgical site. The flexible retractor may include a base, a first retractor appendage coupled to the base wherein the first retractor appendage has a length and lateral sides along its length, a flexible arm coupled to the base at a proximal end of the flexible arm such that a distal end of the flexible arm is movable relative to the base, and a second retractor appendage coupled to the flexible arm at the distal end of the flexible arm wherein the first retractor appendage has a length and lateral sides along its length. The first and second retractor appendages may be aligned substantially along their respective lengths and an access portal to the surgical site is formed between a lateral side of the first retractor appendage and a lateral side of the second retractor appendage.

Still another embodiment of the invention is a transverse retractor. Embodiments of the transverse retractor include an assembly with a frame, a threaded shaft rotatably coupled with the frame, a first carriage coupled with the threaded shaft that is configured to translate along the threaded shaft when the shaft is turned, and a second carriage coupled with the threaded shaft that is configured to translate along the threaded shaft when the shaft is turned. Embodiments of the transverse retractor include a first transverse retractor appendage coupled with the first carriage, wherein the first retractor appendage has a length and lateral sides along its length, and a second transverse retractor appendage coupled with the second carriage, wherein the second retractor appendage has a length and lateral sides along its length. In some embodiments, a first portion of the threaded shaft that is coupled with the first carriage has right-hand threads and a second portion of the threaded shaft that is coupled with the second carriage has left-hand threads such that rotation of the shaft in a first rotational direction causes the first and second transverse retractor appendages to move together simultaneously and rotation of the shaft in a second rotational direction opposite from the first rotational direction causes the first and second transverse retractor appendages to move apart simultaneously.

Another embodiment of the invention is a method of creating an access portal to a surgical site. The method may include introducing a first retractor into the surgical site such that the retractor is in a position to separate tissues along a first axis, and introducing a flexarm retractor into the surgical site such that the flexarm retractor is in a position to separate tissues along a second axis that is substantially transverse to the first axis. The flexarm retractor of some embodiments may include a base, a first retractor appendage coupled to the base, a flexible arm coupled to the base at a proximal end of the flexible arm, and a second retractor appendage coupled to the flexible arm at a distal end of the flexible arm. Method embodiments may also include coupling the flexarm retractor with the first retractor, separating the first retractor appendage from the second retractor appendage to create an access portal to the surgical site, and actuating a control on the flexarm retractor to stiffen the flexible arm to fix the second retractor appendage in a desired location.

Yet another embodiment of the invention is a method of creating an access portal to a surgical site. The method includes introducing a retractor with two appendages into the surgical site such that the retractor is in a position to separate tissues along an axis. The retractor may include mechanisms for switching from a first state where one rotational control moves both appendages simultaneously together or apart along the axis to a second state where the one rotational control moves only one of the appendages along the axis.

BRIEF DESCRIPTION OF THE DRAWINGS

FIG. 10 is an elevation view of internal components of the transverse retractor with a central shaft rotationally engaged with two portions of the threaded shaft.

FIG. 11 is an elevation view of internal components of the transverse retractor with a central shaft rotationally engaged with one portion of the threaded shaft and rotationally disengaged with another portion of the threaded shaft.

DETAILED DESCRIPTION

Figure 1:
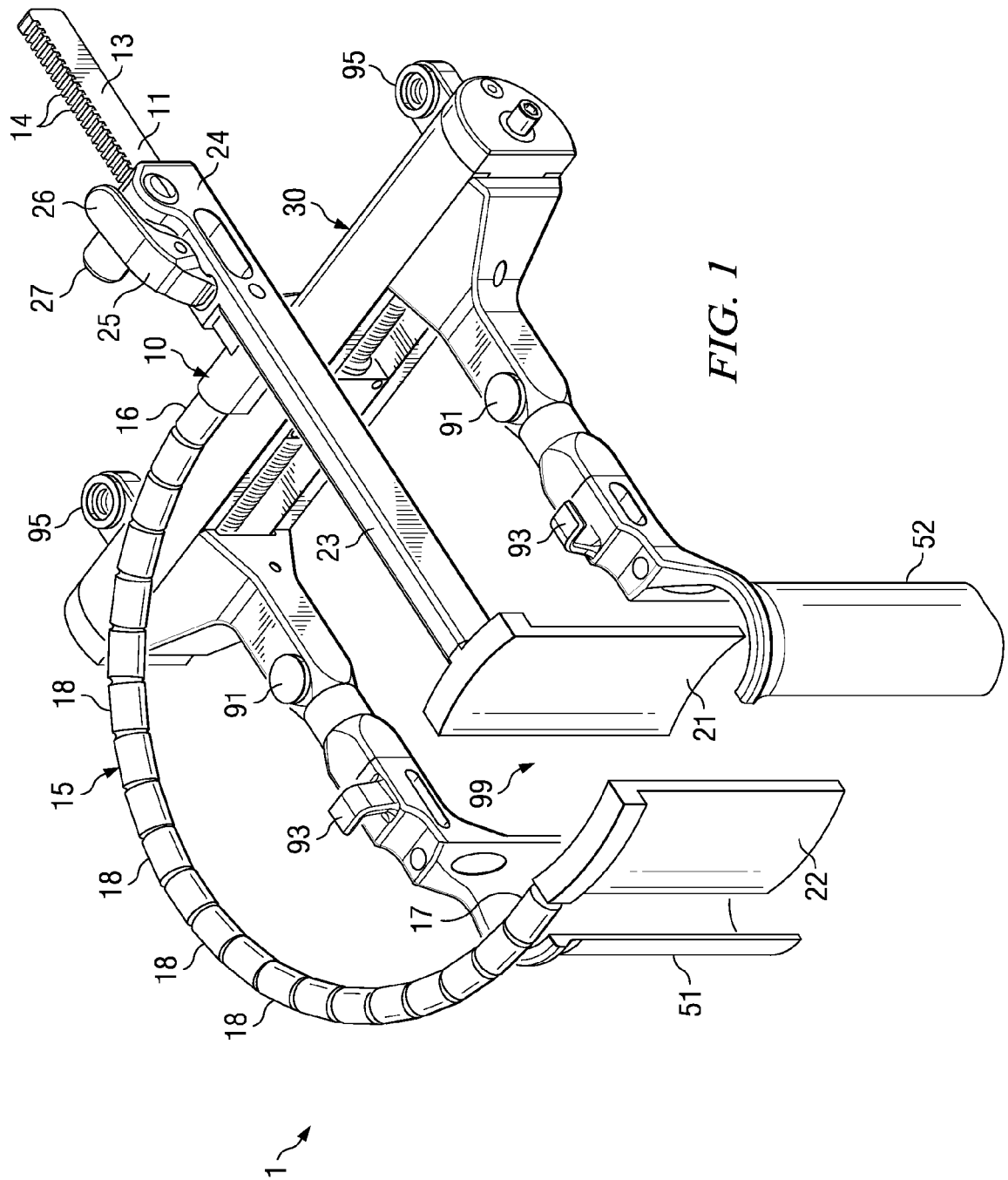
FIG. 1 is a perspective view of a surgical access instrument.

An embodiment of a surgical access instrument 1 is illustrated in FIG. 1. The illustrated surgical access instrument 1 includes a flexarm retractor 10 couple with a transverse retractor 30. An embodiment of the flexarm retractor 10 will be described in more detail with reference to FIGS. 1-5. An embodiment of the transverse retractor will be described in more detail with reference to FIGS. 6-11.

The flexarm retractor 10 illustrated includes a base 11. As most clearly illustrated in FIG. 4, the base 11 of the embodiment shown has a C-shaped body 12 and a rack 13. The C-shaped body 12 is configured to couple with the transverse retractor 30. The coupling between the C-shaped body 12 and the transverse retractor 30 may be an interference fit where the inside of the C-shaped body 12 is pressed against the transverse retractor 30. An interference fit may be adequate to maintain the integrity of the surgical access instrument 1 because forces generated by interactions among components of the surgical access instrument 1, and the retracted tissues may also serve to stabilize the flexarm retractor 10 relative to the transverse retractor 30. The C-shaped body 12 is prevented by the extents of the C-shape from translating up and down relative to the transverse retractor 30. Rotational movement allowed between the C-shaped body 12 and the transverse retractor may be advantageous in surgical procedures where the transverse retractor 30 is first placed in a surgical site, and then the flexarm retractor 10 is added to the construct to complete the surgical access instrument 1. For example, when the transverse retractor 30 is in place in a surgical site, the C-shaped body 12 may be placed against the transverse retractor 30 with one or both of a first retractor appendage 21 and a second retractor appendage 22 rotated up and out of the surgical site. The flexarm retractor may then be rotated about the C-shaped body 12 to insert the first retractor appendage 21 and the second retractor appendage 22 into the surgical site in a desired location.

The coupling between the C-shaped body 12 and the transverse retractor 30 may also be a fixed or pinned coupling in some embodiments. By way of example and without limitation, the coupling may be achieved by welding, may include an adhesive, may include a fastener such as a screw, pin, bolt, rivet, or the like, or may be accomplished through any other effective mechanism.

The rack 13 of the embodiment illustrated in FIGS. 1-5 provides a connection between the base 11 and the first retractor appendage 21 through a bar 23. The bar 23 extends away for the base 11 and terminates at the first retractor appendage 21. The bar 23 shown is slideably coupled to the base 11 such that the first retractor appendage 21 may be moved closer to or more distant from the surgical site relative to the base 11 by sliding the bar 23 relative to the base 11. A pinion assembly 24 couples with the rack 13. The pinion assembly 24 includes a catch 25 that provides a releasable connection between the pinion assembly 24 and one or more teeth 14 of the rack 13. The combination of the teeth 14 and the catch 25 allows for movement of the rack 13 relative to the pinion assembly 24 to be selectively maintained at a desired position. In some embodiments, the catch 25 is biased toward engagement with the teeth 14 such that pressure on a lever end 26 of the catch 25 is required to disengage the catch 25 from the teeth 14. The teeth 14 may be formed such that the pinion assembly 24 ratchets in either direction relative to the base 11. By these or other effective mechanisms, the first retractor appendage 21 may be switched between a free state and a locked state relative to the base 11. The first retractor appendage 21 may also be connected directly to the base 11 in some embodiments without the intervening bar 23 as illustrated. This connection may be fixed or may be releasable.

The pinion assembly 24 also includes a spindle 27 in some embodiments. The spindle 27 includes one or more cogs (not shown) around a perimeter of the spindle 27 that engage with the teeth 14 of the rack 13. By turning the spindle 27, the cogs may be advanced along the teeth 14 to move the rack 13 relative to the pinion assembly 24. The spindle 27 may further include a wing nut, internal hex, external hex, or other opening or component useful in applying torque to the spindle 27 to turn the spindle 27 and move the rack 13 relative to the pinion assembly 24.

Figure 5:
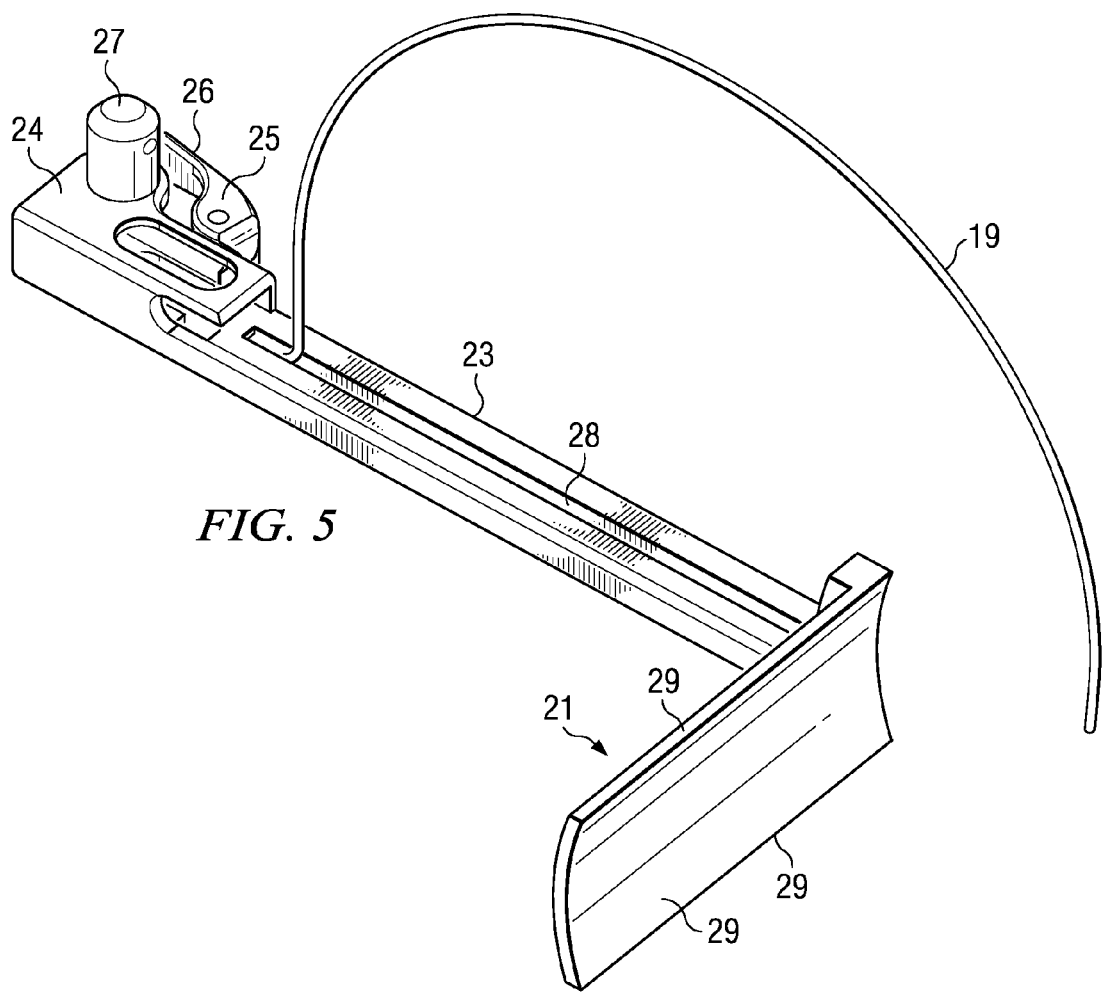
FIG. 5 is a perspective view of the flexarm retractor portion of the surgical access instrument of FIG. 1 with certain components removed.

As illustrated in FIG. 5, the first retractor appendage 21 includes a length extending along its longitudinal axis and lateral sides 29 along its length. The first retractor appendage 21 illustrated has a radius or curve about its longitudinal axis. The curve of the illustrated embodiment has a relatively large radius, but may be significantly reduced in some designs of the invention. For example, the radius may be small to produce essentially a section of a tube approximately the same diameter as the width of the retractor appendage illustrated in FIG. 5. In other embodiments, the retractor appendage may be substantially flat or planar to form a substantially flat blade.

Figure 2:
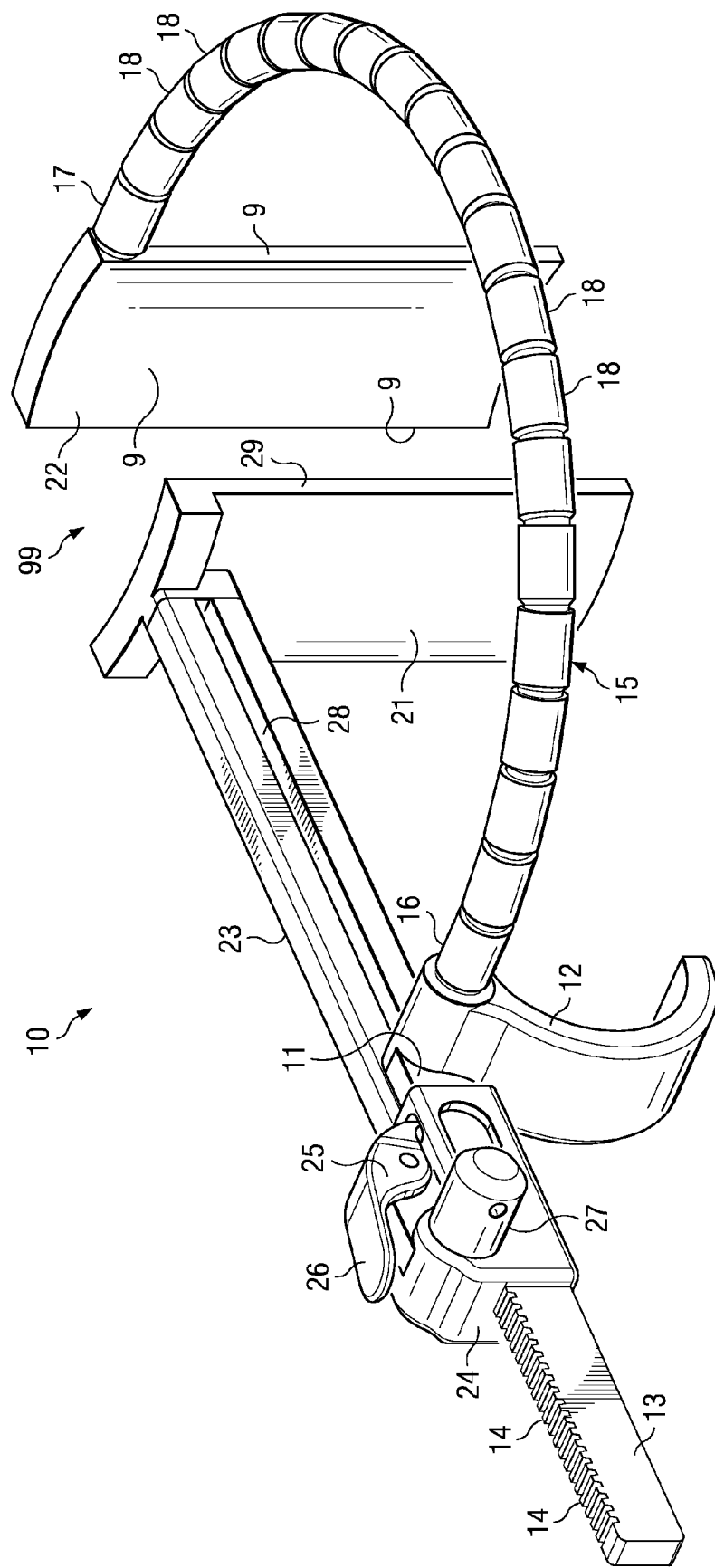
FIG. 2 is a perspective view of the flexarm retractor portion of the surgical access instrument of FIG. 1.
Figure 3:
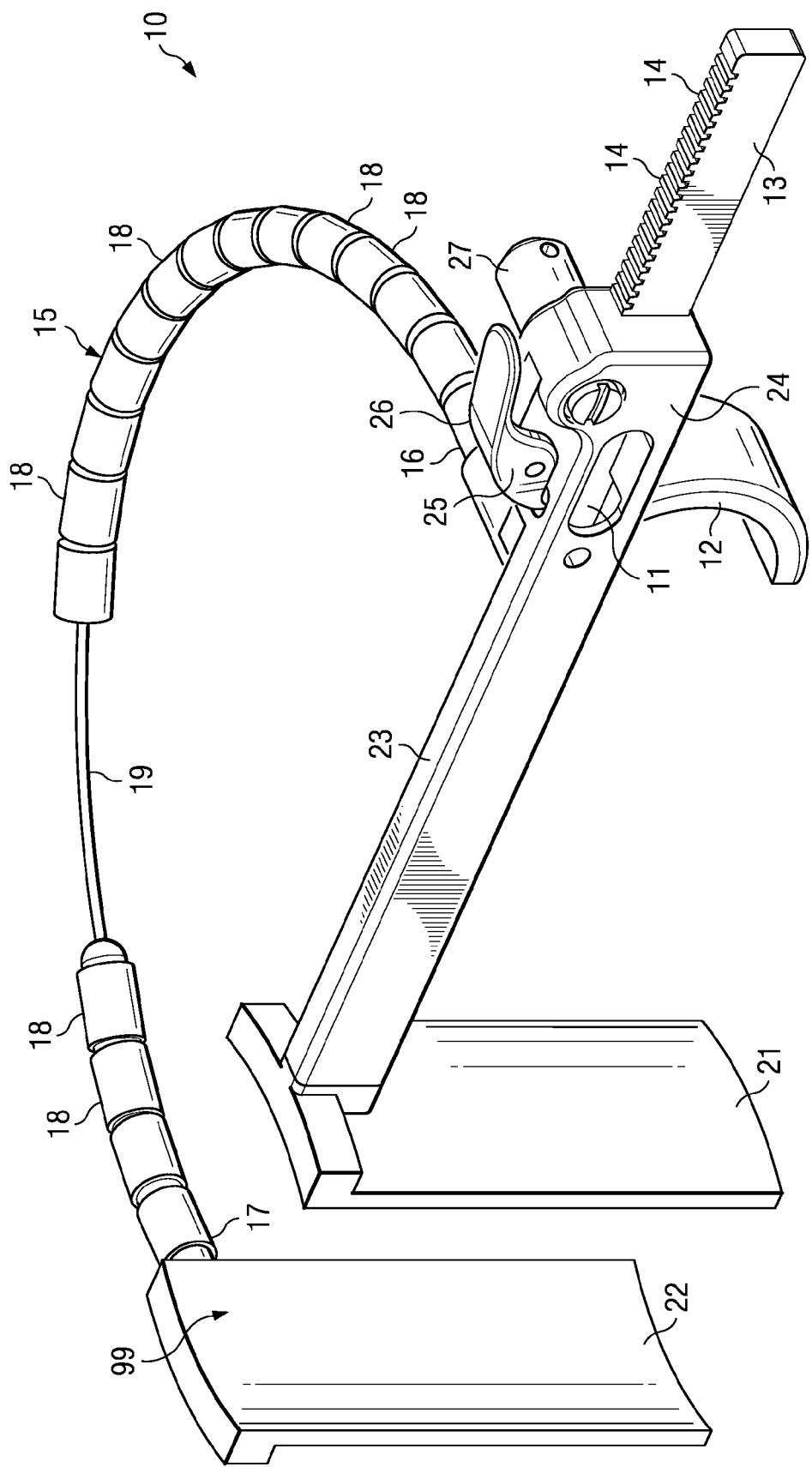
FIG. 3 is a perspective view of the flexarm retractor portion of the surgical access instrument of FIG. 1 with certain components removed.
Figure 4:
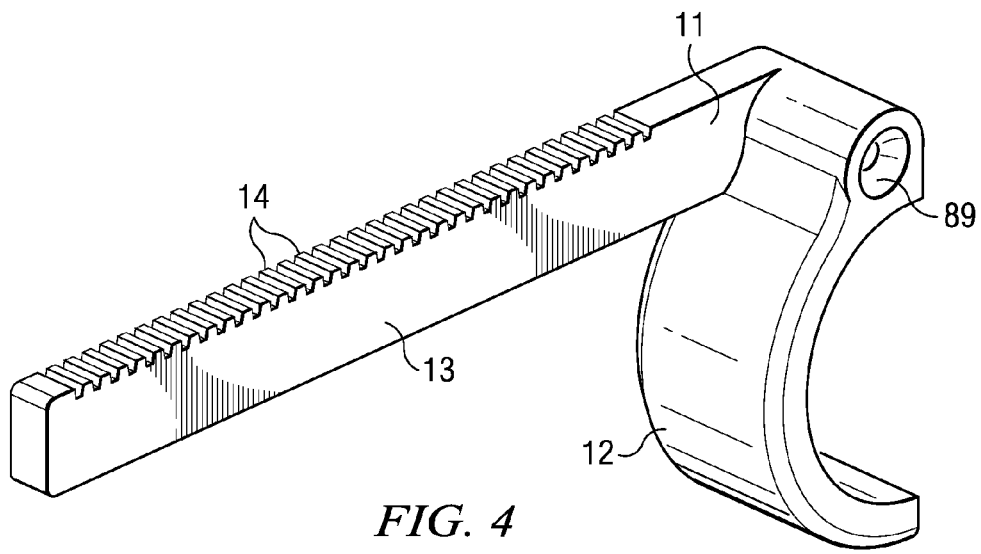
FIG. 4 is a perspective view of the flexarm retractor portion of the surgical access instrument of FIG. 1 with certain components removed.

As illustrated in FIGS. 1-3, a flexible arm 15 is coupled to the base 11 at a proximal end 16 of the flexible arm 15. A distal end 17 of the flexible arm 15 is movable relative to the base 11. In the embodiment shown, multiple cannulated joints 18 interconnect with one another along a curvilinear path to form a continuous cannulated member. In some embodiments, the multiple cannulated joints 18 may interconnect with one another along a linear path. A tensile element 19 is disposed through the cannula of the multiple cannulated joints 18. Several of the cannulated joints 18 are removed from FIG. 3 to show an end of one of the cannulated joints 18 and the tensile element 19. The flexible arm 15 of the illustrated embodiment may have a free state and a locked state relative to the base 11. The free state may exist when the tensile element 19 is loosened and some or all of the cannulated joints 18 are rotatable relative to one another. Another example of a free state is where tension is applied to the tensile element 19 to create some resistance among the cannulated joints 18, but adequate lateral pressure to the flexible arm will result in movement of the flexible arm 15 relative to the base 11. A locked state may exist where significant tension is applied to the tensile element 19 to prevent rotation or movement of the cannulated joints 18 relative to one another. In some embodiments, the second retractor appendage 22 may separately or in conjunction with the flexible arm 15 include a free state and a locked state as a result of tension applied to the tensile element 19 or by other effective mechanisms.

All of the cannulated joints 18 have been removed from the tensile element 19 in the FIG. 5 illustration to show how the tensile element 19 of the embodiment interacts with the bar 23. The tensile element 19 shown fits into a notch 28 in the bar 23 to accommodate movement of the rack 13 next to the bar 23. The tensile element 19 of the embodiment shown in FIGS. 1-5 is threaded through a hole 89 (FIG. 4) in the base 11 and fixed to the bar 23. Consequently, movement of the bar 23 relative to the base 11 by turning of the spindle 27 results in tensioning of the tensile element 19 and locking of the flexible arm 15. Therefore, by common activation of this control, the first retractor appendage 21, the flexible arm 15, and the second retractor appendage 22 may all be switched between a free state and a locked state relative to the base 11. In other embodiments, the bar 23 is independently movable relative to the base 11 and the tensile element 19 is separately able to be tensioned. For example, and without limitation, the notch 28 may pass through the bar 23 in some embodiments, and the tensile element 19 may include a separate control for tightening and loosening the tensile element 19, and therefore the flexible arm 15. In such an embodiment, turning of the spindle 27 results in movement of the first retractor appendage 21 relative to the base 11, and activation of the separate control tightens or loosens the tensile element 19 and the flexible arm 15.

As shown in FIG. 2, the second retractor appendage 22 includes a length extending along its longitudinal axis and lateral sides 9 along its length. The second retractor appendage 22 illustrated has a radius or curve about its longitudinal axis. The curve of the illustrated embodiment has a relatively large radius, but may be significantly reduced in some designs of the invention. For example, the radius may be small to produce essentially a section of a tube approximately the same diameter as the width of the retractor appendages illustrated in FIG. 2. In other embodiments, the retractor appendage may be substantially flat or planar to form a substantially flat blade.

As is shown in combinations of FIGS. 1-3 and 5, the first retractor appendage 21 and the second retractor appendage 22 are aligned substantially along their respective lengths. An access portal 99 to a surgical site is formed between lateral sides 29, 9 of the first retractor appendage 21 and the second retractor appendage 22.

Figure 6:
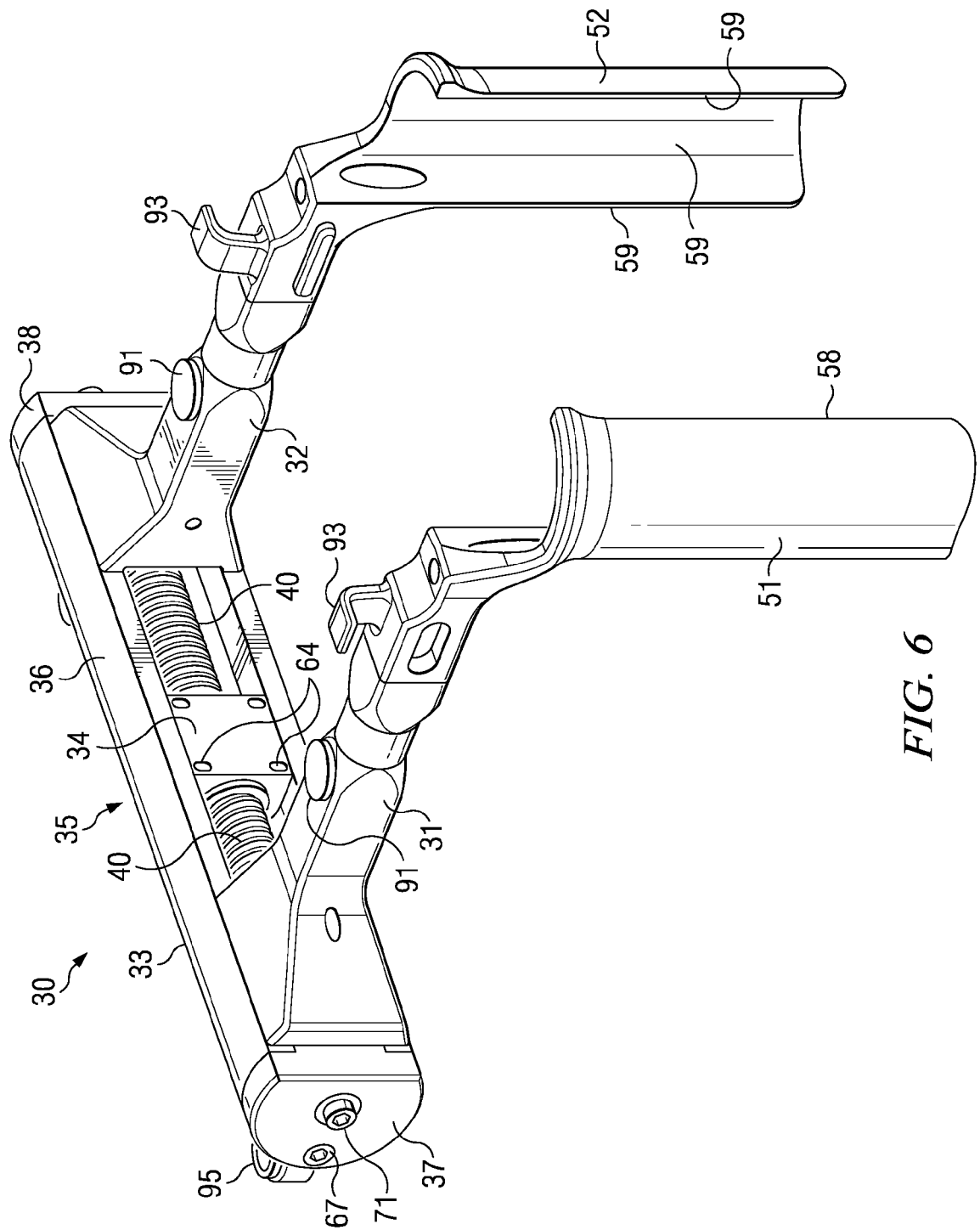
FIG. 6 is a perspective view of the transverse retractor portion of the surgical access instrument of FIG. 1.
Figure 7:
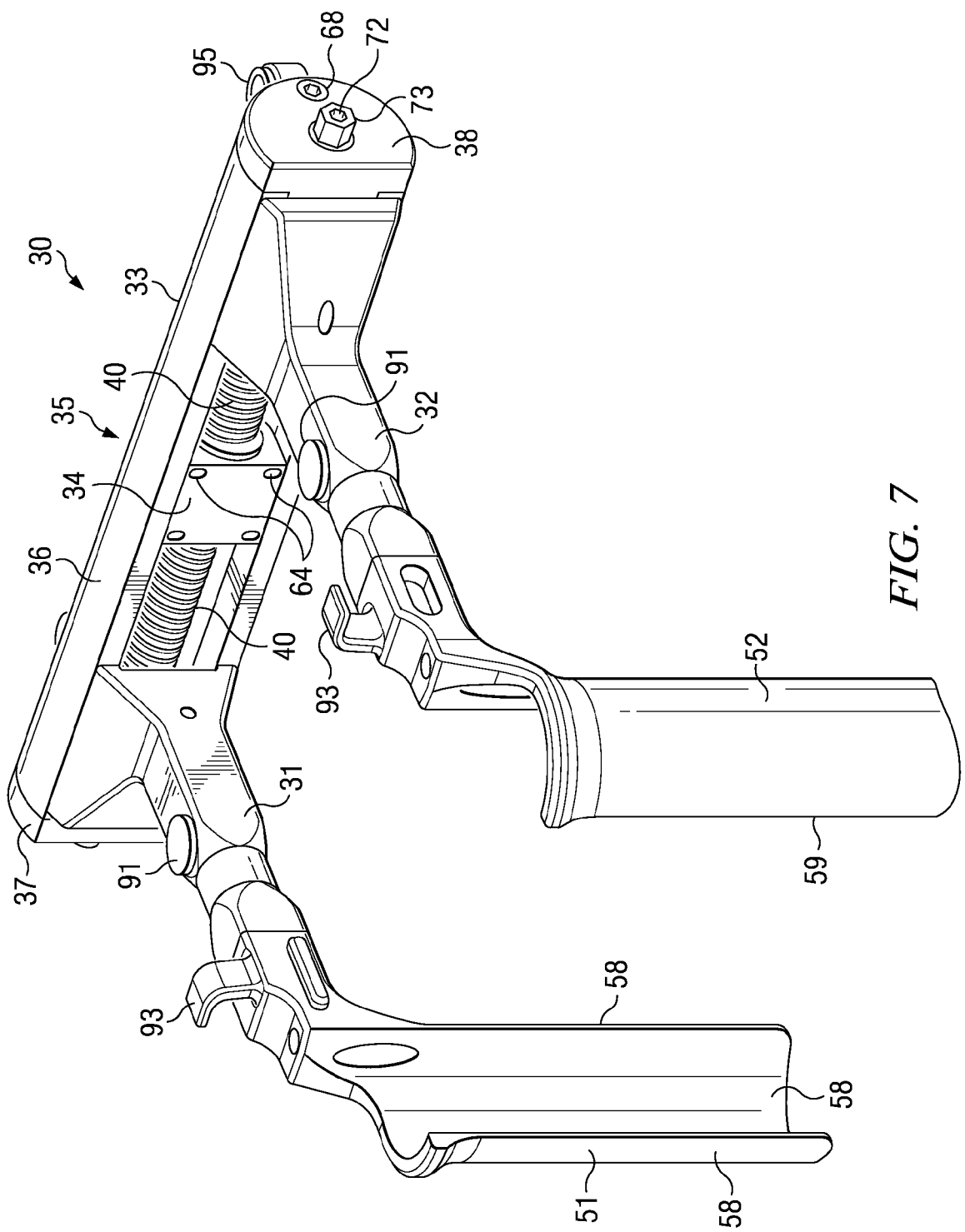
FIG. 7 is a perspective view of the transverse retractor portion of the surgical access instrument of FIG. 1.

In FIGS. 6-11, an embodiment of the transverse retractor 30, including various internal components, is illustrated. The transverse retractor 30 may be coupled to an operating table or other piece of surgical support structure through eyelets 95. An assembly 35 includes a frame 36, a threaded shaft 40 rotatably coupled with the frame 36, a first carriage 31 coupled with the threaded shaft 40 that is configured to translate along the threaded shaft 40 when the threaded shaft 40 is turned, and a second carriage 32 coupled with the threaded shaft 40 that is configured to translate along the threaded shaft 40 when the threaded shaft 40 is turned. The frame 36 illustrated includes a housing 33, a center strut 34, a first end cap 37, and a second end cap 38. The housing 33 of the illustrated embodiment is coupled to the center strut 34 with fasteners (not shown) that extend through fastener openings 63 (FIG. 8) and fastener openings 64 (FIGS. 6 and 7). The first end cap 37 is coupled to the housing 33 with a fastener 67, and the second end cap 38 is coupled to the housing 33 with a fastener 68. In other embodiments, couplings between the components of the frame 36 may be by any effective means, such as but not limited to, welding, application of adhesives, clamping, snap fit components, or with other types of fasteners not specifically listed.

The threaded shaft 40 shown at least in part in each of FIGS. 6-11 couples with and rotates in the frame 36. In the illustrated embodiment, the frame 36 supports the threaded shaft 40 with rotatable couplings in the first end cap 37, the second end cap 38, and at the center strut 34. One or all of the rotatable couplings may include a bushing, a bearing, or a close tolerance fitting of some operable type. The rotatable couplings may include components made from materials other than the materials of the first end cap 37, the second end cap 38, and at the center strut 34, or may be formed as a part of these components. The threaded shaft 40, or portions of the shaft, may be restricted from movement along a longitudinal axis of the threaded shaft 40 by fasteners (not shown) that extend through fastener openings 63 and fastener openings 64, and through grooves 49 (FIGS. 9-11) in the threaded shaft 40.

The threaded shaft 40 may be a unitary piece in some embodiments. In other embodiments, such as the one shown in more detail in FIGS. 9-11, the threaded shaft 40 is composed of multiple components and interact to provide additional functionality to the transverse retractor 30 and surgical access instrument 1. In either type of embodiment, a first portion 41 of the threaded shaft 40 may have right-hand threads that interact with a first carriage 31, and a second portion 42 of the threaded shaft 40 may have left-hand threads that interact with a second carriage 32. With such an arrangement, rotation of the threaded shaft 40 in a first rotational direction will result in the first carriage 31 and the second carriage 32 moving together, or toward one another, simultaneously. Rotation of the threaded shaft 40 in a second rotational direction opposite from the first rotational direction will result in the first carriage 31 and the second carriage 32 moving apart simultaneously.

A first receiver 71 for a rotational tool in the first portion 41 of the threaded shaft 40 is shown in FIG. 6. The first receiver 71 shown is an internal hexagonal shaped opening. Any other functional shape would be acceptable in addition to a hex shape. For example and without limitation, a triangular, square, or other polygonal shape, a star shape, a shape with re-entrant surfaces, and a rounded but non-circular shape would be acceptable. Additionally, in some embodiments an external receiver may be used that extends beyond the surface of the first end cap 37 so that it may be engaged by a rotational tool of any functional shape.

Figure 8:
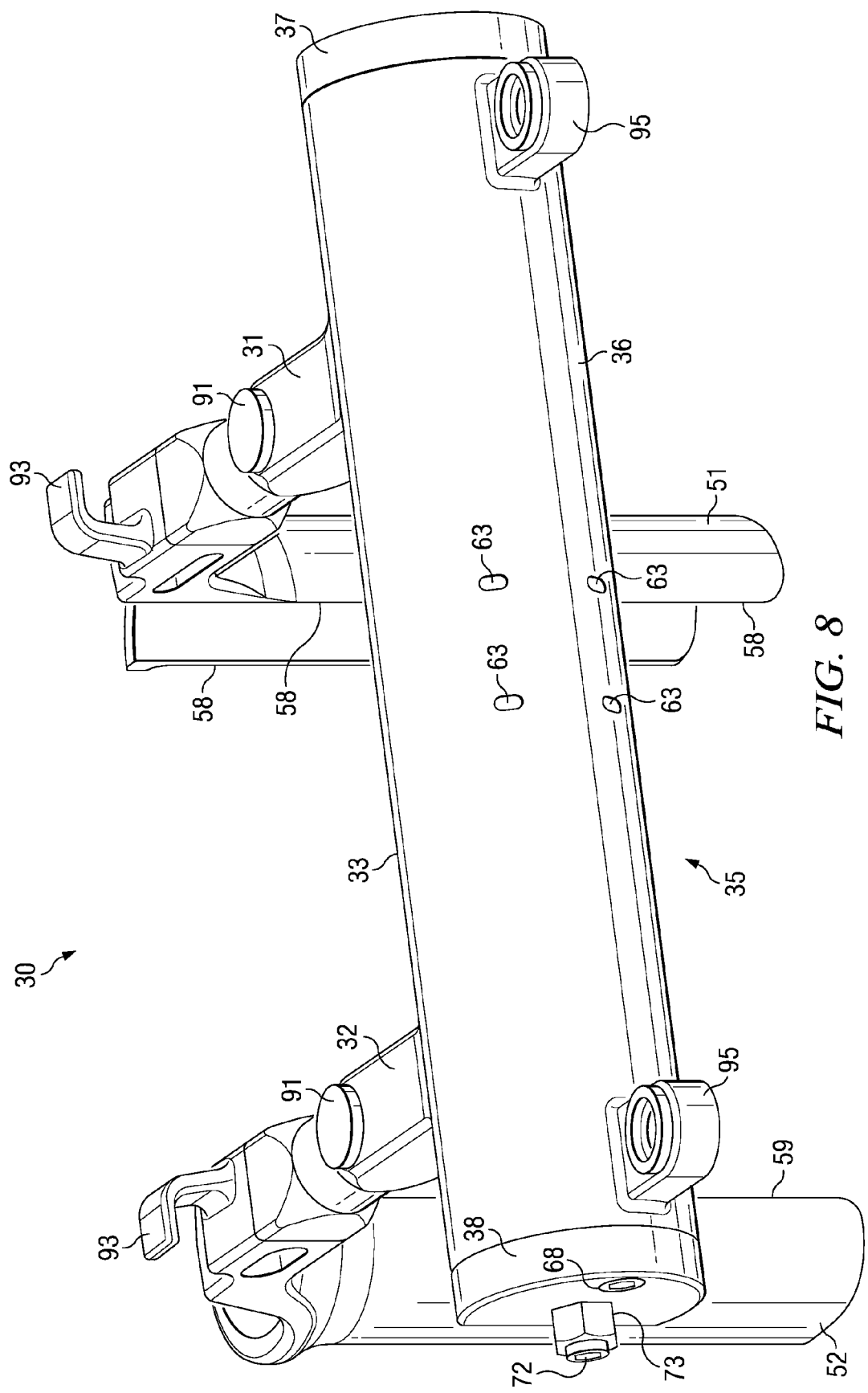
FIG. 8 is a perspective view of the transverse retractor portion of the surgical access instrument of FIG. 1.
Figure 9:
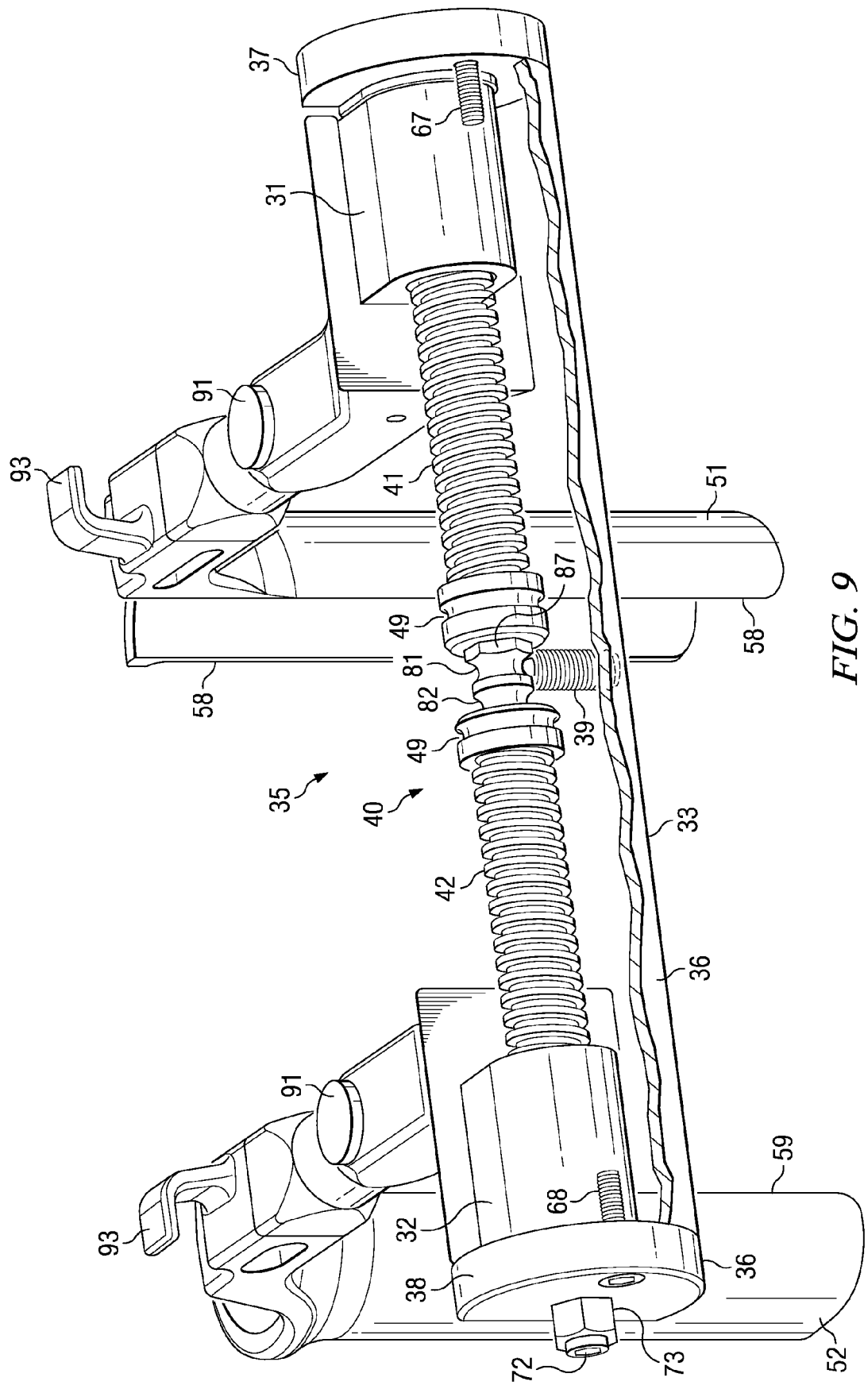
FIG. 9 is a perspective view of the transverse retractor portion as illustrated in FIG. 8 with portions of the transverse retractor cut away to illustrate additional components.

A second receiver for a rotational tool may be embodied in either or both internal receiver 72 and external receiver 73, as illustrated in FIGS. 7-9. The internal receiver 72 shown is an internal hexagonal shaped opening. Any other functional shape would be acceptable in addition to a hex shape. For example and without limitation, a triangular, square, or other polygonal shape, a star shape or other shape with re-entrant surfaces, and a rounded but non-circular shape would be acceptable. The external receiver 73 illustrated is a hexagonal shaped component that extends beyond the surface of the second end cap 38 so that it may be engaged by a rotational tool. In addition to hex shaped, the external receiver may be of any functional shape, for example and without limitation, a triangular, square, or other polygonal shape, a shape with re-entrant surfaces, and a rounded but non-circular shape.

The threaded shaft 40 shown in FIGS. 9-11 includes a central shaft 80 on a common axis and disposed through the first portion 41 of the threaded shaft 40 and the second portion 42 of the threaded shaft 40. In the illustrated embodiment, the first portion 41 and the second portion 42 of the threaded shaft 40 are separate pieces. The central shaft 80 includes a central shaft receiver for accepting a rotational tool used to turn the central shaft 80. In the embodiment shown, the first receiver 71 and internal receiver 72 serve as central shaft receivers for the central shaft 80. In some embodiments, the central shaft receiver may extend outside of the coupling of the threaded shaft 40 with the frame 36 to allow particular rotation capabilities or other operation of the central shaft beyond the frame 36. For the embodiment of FIGS. 9-11, the central shaft 80 may be translated along the common axis relative to the first portion 41 and the second portion 42 of the threaded shaft 40.

FIGS. 9 and 10 show the central shaft 80 in a first position, and FIG. 11 shows the central shaft in a second position relative to the first portion 41 and the second portion 42 of the threaded shaft 40. In the first position, central shaft 80 is rotationally engaged with both the first portion 41 and the second portion 42 of the threaded shaft 40. In the second position, central shaft 80 is rotationally engaged with the first portion 41 of the threaded shaft 40 but disengaged from the second portion 42 of the threaded shaft 40.

A detent 39 is shown in FIGS. 9-11 engaged with the central shaft 80 in two locations. In FIGS. 9 and 10, the detent 39 engages the central shaft 80 in a first indentation 81. In FIG. 11, the detent engages the central shaft 80 in a second indentation 82. The detent 39 is coupled to the housing 33 of the frame 36. The detent 39 of the embodiment shown is biased toward the central shaft 80. The central shaft 80 includes a first key 87 for rotationally engaging with the first portion 41 of the threaded shaft 40 and a second key 88 for rotationally engaging with the second portion 42 of the threaded shaft 40. The first and second keys 87, 88 may be hexagonal shaped, as illustrated. Additionally, and without limitation, their shape may be a triangular, square, or other polygonal shape, a star shape, a shape with re-entrant surfaces, a rounded but non-circular shape, or any other shape or fitting capable of transferring torque.

In operation, when the detent 39 is in the first indention 81, the first key 87 is engaged with a like shaped opening in the first threaded portion 41, and the second key 88 is engaged with a like shaped opening in the second threaded portion 42. Consequently, turning of any of the first receiver 71, the internal receiver 72, or the external receiver 73 will result in turning of both the first threaded portion 41 and the second threaded portion 42, and the first carriage 31 and the second carriage 32 will move simultaneously.

The central shaft 80 may be translated along the common axis relative to the first portion 41 and the second portion 42 of the threaded shaft 40 by applying a force F to the central shaft 80, as noted in FIG. 10. FIG. 11 illustrates the result of applying adequate force F to the central shaft 80 to overcome the biasing force of the detent 39 and thereby moving the central shaft 80 to the second position such that the detent 39 is located in the second indentation 82 rather than the first indentation 81. As seen in FIG. 11, the central shaft 80 is rotationally engaged with the first portion 41 of the threaded shaft 40 by engagement with first key 87. However, the central shaft 80 is rotationally disengaged from the second portion 42 of the threaded shaft 40 at second key 88. Consequently, turning of the first receiver 71 or the internal receiver 72 will result in turning the first threaded portion 41 and moving the first carriage 31, but not in turning the second threaded portion 42 and moving the second carriage 32. Turning of the external receiver 73 will result in turning the second threaded portion 42 and moving the second carriage 32, but not in turning the first threaded portion 41 and moving the first carriage 31. With this mechanism, it is possible to independently control either the first carriage 31 or the second carriage 32 from a single end of the transverse retractor 30. This feature may be useful in expediently controlling the transverse retractor 30 without repositioning the device relative to a patient.

In the transverse retractor 30 shown in FIGS. 6-9, a first transverse retractor appendage 51 is coupled with the first carriage 31. The first retractor appendage 51 has a length and lateral sides 58 along its length. The transverse retractor 30 also includes a second transverse retractor appendage 52 coupled with the second carriage 32. The second transverse retractor appendage 52 has a length and lateral sides 59 along its length. The coupling between each of the transverse retractor appendages 51, 52 and respective carriages 31, 32 of the illustrated embodiment is a rotatable coupling. In some embodiments, pressing of a button 91 rotationally releases each transverse retractor appendage 51, 52, relative to the respective carriages 31, 32 allowing for relative rotation of the retractor appendages 51, 52. Releasing the button 91 may lock each transverse retractor appendage 51, 52, relative to the respective carriages 31, 32 near a position of the transverse retractor appendage 51, 52 at the time its respective button 91 is released. Instrument hooks 93 on each of the transverse retractor appendages 51, 52, are provided with some embodiments to facilitate attaching an instrument to apply rotational force to the transverse retractor appendages 51, 52. Rotating the transverse retractor appendages 51, 52 may provide better access to a surgical site, including a larger subcutaneous working channel.

The first transverse retractor appendage 51 illustrated has a radius or curve about its longitudinal axis. The curve of the illustrated embodiment is a relatively small radius, but may be significantly enlarged in some designs of the invention. For example, the radius may be enlarged to produce a slightly curved appendage as illustrated in FIGS. 2 and 3. In other embodiments, the transverse retractor appendage may be substantially flat or planar to form a substantially flat blade.

The second transverse retractor appendage 52 illustrated has a radius or curve about its longitudinal axis. The curve of the illustrated embodiment is a relatively small radius, but may be significantly enlarged in some designs of the invention. For example, the radius may be enlarged to produce a slightly curved appendage as illustrated in FIGS. 2 and 3. In other embodiments, the transverse retractor appendage may be substantially flat or planar to form a substantially flat blade.

As is shown in combinations of FIGS. 1, 2, and 6, the first retractor appendage 21, the second retractor appendage 22, the first transverse retractor appendage 51, and the second transverse retractor appendage 52 are configured to be aligned substantially along their respective lengths and an access portal 99 to the surgical site is formed among the lateral sides 29, 9, 58, 59 of the first retractor appendage 21, the second retractor appendage 22, the first transverse retractor appendage 51, and the second transverse retractor appendage 52.

Figure 12:
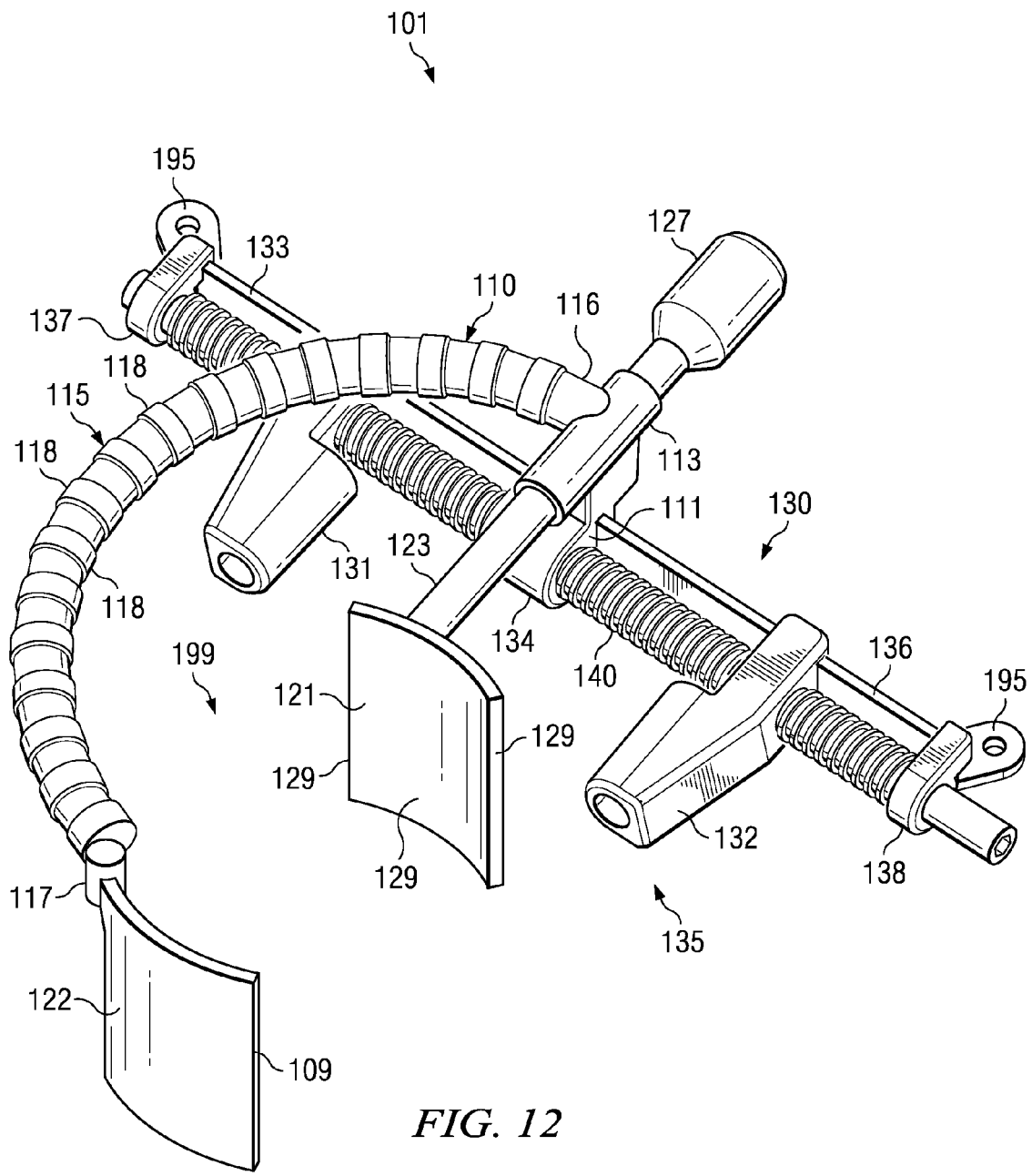
FIG. 12 is a perspective view of a surgical access instrument.

Another embodiment of a surgical access instrument 101 is illustrated in FIG. 12. The illustrated surgical access instrument 101 includes a flexarm retractor 110 couple with a transverse retractor 130. The flexarm retractor 110 illustrated includes a base 111. The base 111 of the embodiment shown is configured to couple with the transverse retractor 130 along a housing 133 of a frame 136 of the transverse retractor 130. The coupling between the base 111 and the transverse retractor 130 may also be an interference fit or a fixed or pinned coupling in some embodiments. By way of example and without limitation, the coupling may be achieved by welding, may include an adhesive, may include a fastener such as a screw, pin, bolt, rivet, or the like, or may be accomplished through any other effective mechanism.

A rack 113 of the illustrated embodiment provides a connection between the base 111 and the first retractor appendage 121 through a bar 123. The bar 123 extends away for the base 111 and terminates at the first retractor appendage 121. The bar 123 shown is fixed to the base 111. In other embodiments, the bar 123 may be slideably coupled to the base 111 so that the first retractor appendage 121 may be moved closer to or more distant from the surgical site relative to the base 111 by sliding the bar 123 relative to the base 111.

The first retractor appendage 121 includes a length extending along its longitudinal axis and lateral sides 129 along its length. The first retractor appendage 121 illustrated has a radius or curve about its longitudinal axis. The curve of the illustrated embodiment has a relatively large radius, but may be significantly reduced in some designs of the invention. For example, the radius may be small to produce essentially a section of a tube. In other embodiments, the retractor appendage may be substantially flat or planar to form a substantially flat blade.

A flexible arm 115 is coupled to the base 111 at a proximal end 116 of the flexible arm 115. A distal end 117 of the flexible arm 115 is movable relative to the base 111. In the embodiment shown, multiple cannulated joints 118 interconnect with one another along a curvilinear path to form a continuous cannulated member. In some embodiments, the multiple cannulated joints 118 may interconnect with one another along a linear path. A tensile element (not shown) may be disposed through the cannula of the multiple cannulated joints 118. The flexarm retractor 110 includes a control 127 in some embodiments attached to the tensile element to tighten and release the tensile element. The flexible arm 115 of the illustrated embodiment may have a free state and a locked state relative to the base 111. The free state may exist when the tensile element is loosened and some or all of the cannulated joints 118 are rotatable relative to one another. Another example of a free state is where tension is applied to the tensile element to create some resistance between the cannulated joints 118, but adequate lateral pressure to the flexible arm 115 will result in movement of the flexible arm 115 relative to the base 111. A locked state may exist where significant tension is applied to the tensile element to prevent rotation or movement of the cannulated joints 118 relative to one another. In some embodiments, the second retractor appendage 122 may separately or in conjunction with the flexible arm 115 include a free state and a locked state as a result of tension applied to the tensile element or by other effective mechanisms.

In some embodiments, the control 127 also releases and locks the bar 123 relative to the base 111. Therefore, by common activation of the control 127, the first retractor appendage 121, the flexible arm 115, and the second retractor appendage 122 may all be switched between a free state and a locked state relative to the base 111. In other embodiments, the bar 123 is independently movable relative to the base 111 and the tensile element is separately able to be tensioned.

The second retractor appendage 122 includes a length extending along its longitudinal axis and lateral sides 109 along its length. The second retractor appendage 122 illustrated has a radius or curve about its longitudinal axis. The curve of the illustrated embodiment has a relatively large radius, but may be significantly reduced in some designs of the invention. For example, the radius may be small to produce essentially a section of a tube. In other embodiments, the retractor appendage may be substantially flat or planar to form a substantially flat blade.

As is shown in FIG. 12, the first retractor appendage 121 and the second retractor appendage 122 are aligned substantially along their respective lengths. An access portal 199 to a surgical site is formed between lateral sides 129, 109 of the first retractor appendage 121 and the second retractor appendage 122.

The transverse retractor 130 may be coupled to an operating table or other piece of surgical support structure through eyelets 195. An assembly 135 includes a frame 136, a threaded shaft 140 rotatably coupled with the frame 136, a first carriage 131 coupled with the threaded shaft 140 that is configured to translate along the threaded shaft 140 when the threaded shaft is turned, and a second carriage 132 coupled with the threaded shaft 140 that is configured to translate along the threaded shaft 140 when the shaft is turned. The frame 136 illustrated includes a housing 133, a center strut 134, a first end cap 137, and a second end cap 138. The housing 133 of the illustrated embodiment is coupled to the center strut 134. The first end cap 137 is coupled to the housing 133, and the second end cap 138 is coupled to the housing 133. Couplings between the components of the frame 136 may be by any effective means, such as but not limited to, welding, application of adhesives, clamping, snap fit components, or with any type of fastener.

The threaded shaft 140 shown couples with and rotates in the frame 136. In the illustrated embodiment, the frame 136 supports the threaded shaft 140 with rotatable couplings in the first end cap 137, the second end cap 138, and at the center strut 134. One or all of the rotatable couplings may include a bushing, a bearing, or a close tolerance fitting or some operable type. The rotatable couplings may include components made from materials other than the materials of the first end cap 137, the second end cap 138, and at the center strut 134, or may be formed as a part of these components.

The threaded shaft 140 may be a unitary piece in some embodiments. In other embodiments, the threaded shaft 140 is composed of multiple components and interacts to provide additional functionality to the transverse retractor 130 and surgical access instrument 101 as, for example, detailed with regard to the transverse retractor 30 above. A first portion of the threaded shaft 140 may have right-hand threads that interact with a first carriage 131, and a second portion of the threaded shaft 140 may have left-hand threads that interact with a second carriage 132. With such an arrangement, rotation of the threaded shaft 140 in a first rotational direction will result in the first carriage 131 and the second carriage 132 moving together, or toward one another, simultaneously. Rotation of the threaded shaft 140 in a second rotational direction opposite from the first rotational direction will result in the first carriage 131 and the second carriage 132 moving apart simultaneously.

In embodiments of the transverse retractor 130, various transverse retractor appendages may be coupled to one or both of the first carriage 131 and the second carriage 132. Transverse retractor appendages 51, 52 detailed above are non-limiting examples of devices that may be used in conjunction with the first carriage 131 and the second carriage 132.

Embodiments of the invention include a portal means for accessing a surgical site. The portal or access means may include a first retractor means for retracting tissue in a first direction. Additionally, the portal means may include a flexarm retractor means for retracting tissue in a second direction substantially transverse to the first direction. The flexarm retractor may further be capable of assuming a flexible state and a rigid state along its length in response to the actuation of a single control.

All or a portion of the surgical access instruments of embodiments of the disclosed invention may be made of any biocompatible material. For example and without limitation, materials of the surgical access instruments may include non-reinforced polymers, carbon-reinforced polymer composites, PEEK and PEEK composites, low density polyethylene, shape-memory alloys, titanium, titanium alloys, cobalt chrome alloys, stainless steel, ceramics and combinations thereof. Material of the surgical access instruments may be radiopaque or may be radiolucent. If radiolucent, the instruments may include markers placed in certain components of the instruments to provide for guidance of the instruments under radiographic imaging.

Another embodiment of the invention is a method of creating an access portal to a surgical site. The method includes introducing a first retractor into the surgical site such that the retractor is in a position to separate tissues along a first axis. The first retractor may include mechanisms for independently moving two retractor appendages or blades along the first axis. The method also includes introducing a flexarm retractor into the surgical site such that the flexarm retractor is in a position to separate tissues along a second axis that is substantially transverse to the first axis. The flexarm retractor of some embodiments includes a base, a first retractor appendage coupled to the base, a flexible arm coupled to the base at a proximal end of the flexible arm, and a second retractor appendage coupled to the flexible arm at a distal end of the flexible arm. The method further includes coupling the flexarm retractor with the first retractor, separating the first retractor appendage from the second retractor appendage to create an access portal to the surgical site, and actuating a control on the flexarm retractor to stiffen the flexible arm to fix the second retractor appendage in a desired location. In some embodiments, actuating the control on the flexarm retractor to stiffen the flexible arm also locks the first retractor appendage relative to the base. Embodiments of the method may further include operating the first retractor to separate tissues along the first axis.

Still another embodiment of the invention is a method of creating an access portal to a surgical site. The method includes introducing a retractor with two appendages into the surgical site such that the retractor is in a position to separate tissues along an axis. The retractor may include mechanisms for switching from a first state where one rotational control moves both appendages simultaneously together or apart along the axis to a second state where the one rotational control moves only one of the appendages along the axis. In some embodiments, the mechanism for switching between the first and second states requires application of a force to a portion of the retractor along the axis. In some embodiments, application of another force in a direction substantially opposite to the direction of the first force results in a return to the first state where one rotational control moves both appendages simultaneously together or apart along the axis.

Various method embodiments of the invention are described herein with reference to particular devices. However, in some circumstances, each disclosed method embodiment may be applicable to each of the devices, or to some other device operable as disclosed with regard to the various method embodiments.

Terms such as proximal, distal, near, lower, upper, lateral, and the like have been used herein to note relative positions. However, such terms are not limited to specific coordinate orientations, but are used to describe relative positions referencing particular embodiments. Such terms are not generally limiting to the scope of the claims made herein.

While embodiments of the invention have been illustrated and described in detail in the disclosure, the disclosure is to be considered as illustrative and not restrictive in character. All changes and modifications that come within the spirit of the invention are to be considered within the scope of the disclosure.

What is claimed is:

1. A surgical access instrument comprising:
    a flexarm retractor comprising:
        a base,
        a first retractor appendage coupled to the base wherein the first retractor appendage has a length and lateral sides along its length,
        a flexible arm coupled to the base at a proximal end of the flexible arm such that a distal end of the flexible arm is movable relative to the base, and
        a second retractor appendage coupled to the flexible arm at the distal end of the flexible arm wherein the second retractor appendage has a length and lateral sides along its length; and
    a transverse retractor coupled to the base of the flexarm retractor comprising:
        an assembly comprising:
            a frame,
            a threaded shaft rotatably coupled with the frame,
            a first carriage coupled with the threaded shaft that is configured to translate along the threaded shaft when the shaft is turned, and
            a second carriage coupled with the threaded shaft that is configured to translate along the threaded shaft when the shaft is turned,
        a first transverse retractor appendage coupled with the first carriage, wherein the first retractor appendage has a length and lateral sides along its length, and a second transverse retractor appendage coupled with the second carriage, wherein the second retractor appendage has a length and lateral sides along its length;

wherein the first retractor appendage, the second retractor appendage, the first transverse retractor appendage, and the second transverse retractor appendage are configured to be aligned substantially along their respective lengths and an access portal to the surgical site is formed among a lateral side of the first retractor appendage, a lateral side of the second retractor appendage, a lateral side of the first transverse retractor appendage, and a lateral side of the second transverse retractor appendage;

wherein a first portion of the threaded shaft that is coupled with the first carriage has right-hand threads and a second portion of the threaded shaft that is coupled with the second carriage has left-hand threads such that rotation of the threaded shaft in a first rotational direction causes the first and second transverse retractor appendages to move together simultaneously and rotation of the threaded shaft in a second rotational direction opposite from the first rotational direction causes the first and second transverse retractor appendages to move apart simultaneously;

wherein the threaded shaft comprises a central shaft on a common axis with and disposed through the first portion of the threaded shaft and the second portion of the threaded shaft, and wherein the first portion of the threaded shaft and the second portion of the threaded shaft are separate pieces;

wherein the central shaft may be translated along the common axis relative to the first portion of the threaded shaft and the second portion of the threaded shaft; and wherein translating the central shaft in a first direction results in the central shaft being rotationally disengaged from the second portion of the threaded shaft.

2. The instrument of claim 1 wherein one or more of the first retractor appendage, the second retractor appendage, the first transverse retractor appendage, and the second transverse retractor appendage is a substantially flat blade.

3. The instrument of claim 1 wherein one or more of the first retractor appendage, the second retractor appendage, the first transverse retractor appendage, and the second transverse retractor appendage is a member curved about a longitudinal axis of the respective retractor appendage.

4. The instrument of claim 1 wherein the first retractor appendage includes a free state and a locked state relative to the base.

5. The instrument of claim 1 wherein the flexible arm comprises:
multiple cannulated joints that interconnect with one another along a linear or curvilinear path to form a continuous cannulated member, and
a tensile element disposed through the cannula of the multiple cannulated joints.

6. The instrument of claim 1 wherein the flexible arm and the second retractor appendage each include a free state and a locked state relative to the base.

7. The instrument of claim 1, further comprising a control to switch the flexible arm and the second retractor appendage both between a free state and a locked state relative to the base with a common actuation of the control.

8. The instrument of claim 1, further comprising a control to switch the first retractor appendage, the flexible arm, and the second retractor appendage all between a free state and a locked state relative to the base with a common actuation of the control.

9. A transverse retractor comprising:
an assembly comprising:
a frame,
a threaded shaft rotatably coupled with the frame,
a first carriage coupled with the threaded shaft that is configured to translate along the threaded shaft when the shaft is turned, and
a second carriage coupled with the threaded shaft that is configured to translate along the threaded shaft when the shaft is turned;
a first transverse retractor appendage coupled with the first carriage, wherein the first retractor appendage has a length and lateral sides along its length; and
a second transverse retractor appendage coupled with the second carriage, wherein the second retractor appendage has a length and lateral sides along its length;
wherein a first portion of the threaded shaft that is coupled with the first carriage has right-hand threads and a second portion of the threaded shaft that is coupled with the second carriage has left-hand threads such that rotation of the threaded shaft in a first rotational direction causes the first and second transverse retractor appendages to move together simultaneously and rotation of the threaded shaft in a second rotational direction opposite from the first rotational direction causes the first and second transverse retractor appendages to move apart simultaneously;
wherein the threaded shaft comprises a central shaft on a common axis with and disposed through the first portion of the threaded shaft and the second portion of the threaded shaft, and wherein the first portion of the threaded shaft and the second portion of the threaded shaft are separate pieces;
wherein the central shaft may be translated along the common axis relative to the first portion of the threaded shaft and the second portion of the threaded shaft; and
wherein translating the central shaft in a first direction results in the central shaft being rotationally disengaged from the second portion of the threaded shaft, but rotationally engaged with the first portion of the threaded shaft.

10. The transverse retractor of claim 9 wherein the frame includes a housing disposed around at least a majority of a perimeter of the threaded shaft, and wherein the frame supports the threaded shaft with rotatable couplings at each longitudinal end of the housing.

11. The transverse retractor of claim 9 wherein the first portion of the threaded shaft includes a first receiver for a rotation tool.

12. The transverse retractor of claim 9 wherein the second portion of the threaded shaft includes a second receiver for a rotation tool.

13. The transverse retractor of claim 9 wherein the central shaft includes a central shaft receiver for a rotation tool.

* * * * *